United States Patent
Benedict

(10) Patent No.: US 9,439,977 B2
(45) Date of Patent: Sep. 13, 2016

(54) METHODS AND COMPOSITIONS FOR TREATMENT OF INTERFERON-RESISTANT TUMORS

(75) Inventor: William F. Benedict, The Woodlands, TX (US)

(73) Assignee: FKD Therapies Oy, Kuopio (FI)

(*) Notice: Subject to any disclaimer, the term of this patent is extended or adjusted under 35 U.S.C. 154(b) by 1494 days.

(21) Appl. No.: 12/706,625

(22) Filed: Feb. 16, 2010

(65) Prior Publication Data

US 2010/0266547 A1    Oct. 21, 2010

Related U.S. Application Data

(63) Continuation of application No. 11/009,689, filed on Dec. 10, 2004, now Pat. No. 7,691,822.

(60) Provisional application No. 60/528,525, filed on Dec. 10, 2003.

(51) Int. Cl.

| C12N 15/11 | (2006.01) |
|---|---|
| A61K 48/00 | (2006.01) |
| A61K 9/00 | (2006.01) |
| A61K 9/127 | (2006.01) |
| A61K 38/21 | (2006.01) |
| C07K 14/56 | (2006.01) |
| C12N 15/86 | (2006.01) |

(52) U.S. Cl.
CPC ......... *A61K 48/0008* (2013.01); *A61K 9/0034* (2013.01); *A61K 9/1271* (2013.01); *A61K 38/212* (2013.01); *A61K 48/00* (2013.01); *C07K 14/56* (2013.01); *C12N 15/86* (2013.01); *C12N 2710/10343* (2013.01)

(58) Field of Classification Search
CPC .................................................... C12N 15/11
See application file for complete search history.

(56) References Cited

U.S. PATENT DOCUMENTS

| 5,120,316 A | 6/1992 | Morales et al. |
|---|---|---|
| 5,552,309 A | 9/1996 | March |
| 5,602,023 A | 2/1997 | Csatary |
| 5,789,244 A | 8/1998 | Heidrun et al. |
| 5,804,566 A | 9/1998 | Carson et al. |
| 6,066,624 A | 5/2000 | Woo et al. |
| 6,165,779 A | 12/2000 | Engler et al. |
| 6,207,454 B1 | 3/2001 | Zsebo et al. |
| 6,210,939 B1 | 4/2001 | Gregory et al. |
| 6,312,681 B1 | 11/2001 | Engler et al. |
| 6,392,069 B2 | 5/2002 | Engler et al. |
| 7,002,027 B1 | 2/2006 | Engler et al. |
| 7,355,056 B2 | 4/2008 | Connor et al. |
| 7,534,769 B2 | 5/2009 | Engler et al. |
| 2002/0111502 A1 | 8/2002 | Engler et al. |
| 2003/0170216 A1 | 9/2003 | Ihnat et al. |
| 2003/0211598 A1 | 11/2003 | Engler et al. |
| 2004/0014709 A1 | 1/2004 | Engler et al. |
| 2005/0025742 A1 | 2/2005 | Engler et al. |
| 2005/0287119 A1 | 12/2005 | Benedict |
| 2006/0199782 A1 | 9/2006 | Engler et al. |
| 2007/0249043 A1 | 10/2007 | Mayall |

FOREIGN PATENT DOCUMENTS

| EP | 0331635 A2 | 8/1989 |
|---|---|---|
| WO | WO 97/05209 A1 | 2/1997 |
| WO | WO 97/25072 A1 | 7/1997 |
| WO | WO 98/17801 A1 | 4/1998 |
| WO | WO 03/053365 A2 | 7/2003 |
| WO | WO 03/053365 A3 | 7/2003 |
| WO | WO 03/073998 A2 | 9/2003 |
| WO | WO 03/073998 A3 | 9/2003 |

OTHER PUBLICATIONS

Torti et al. (J. Clin. Oncol. 1988; 6(3):476-83).*
Hand et al. (Anticancer Drugs 1993; 4(3):365-8).*
Adam, Liana, et al. "Adenoviral Mediated Interferon-α 2b Gene Therapy Suppresses the Pro-Angiogenic Effect of Vascular Endothelial Growth Factor in Superficial Bladder Cancer," The Journal of Urology, 2007, vol. 177, pp. 1900-1906.
Ahmed et al., *Cancer Gene Therapy*, 8(10):788-795 (2001).
Ahmed et al., *Hum. Gene Ther.*, 10:77-78 (1999).
Ahmed et al., *Journal of Interferon and Cytokine Research*, 21(6):399-408 (2001).
Associated Press, "One Way to Kill Cancer: Give a Cold," *The Augusta Chronicle*, May 20, 1997, accessed by PTO at <http://www.cnn.com> on May 22, 1997.
Belldegrun et al., *J. Urol.*, 159:1793-1801 (1998).
Benedict et al., *Molecular Therapy*, 10(3):525-532 (2004).
Chester, J.D. et al., "Adenovirus-mediated gene therapy for bladder cancer: efficient gene delivery to normal and malignant human urothelial cells in vitro and ex vivo," *Gene Therapy*, 2003, vol. 10, pp. 172-179.
Connor et al., *Gene Ther.*, 8:41-48 (2001).
Croyle, M.A. et al., "Development of formulations that enhance physical stability of viral vectors for gene therapy," *Gene Therapy*, 2001, vol. 8, pp. 1281-1290.
Crystal, R.G. et al., "Transfer of Genes to Humans: Early Lessons and Obstacles to Success," *Science*, 1995, vol. 270, pp. 404-410.
Culver, K.W. et al., "Gene Therapy for Cancer," *Trends in Genetics*, May 1994, vol. 10, No. 5, pp. 174-178.
Dalbagni et al., *Urol. Clin. North Am.*, 27(1):137-146 (2000).
Freidmann, T., "Gene Therapy of Cancer Through Restoration of Tumor-Suppressor Functions?" *Cancer*, 1992, vol. 70, pp. 1810-1817.

(Continued)

*Primary Examiner* — Jon E Angell
(74) *Attorney, Agent, or Firm* — Pharmaceutical Patent Attorneys, LLC

(57) ABSTRACT

The present invention provides a method for the treatment of interferon resistant tumors through the use of recombinant vectors encoding interferon species. In particular it is noted that interferon species provided by recombinant vectors possesses properties not associated with the recombinantly produced interferon proteins. The present invention further provides compositions useful in the treatment of interferon resistant tumors using recombinant vectors encoding interferons.

13 Claims, 5 Drawing Sheets

(56) References Cited

OTHER PUBLICATIONS

Gardlik, R. et al., "Vectors and Delivery Systems in Gene Therapy," *Medical Science Monitor*, 2005, vol. 11, No. 4, pp. RA110-RA121.
Glashan, *The Journal of Urology*, 144:658-661 (1990).
Goncalves, M.A.F.V., "A Concise Peer Into the Background, Initial Thoughts and Practices of Human Gene Therapy," *BioEssays*, 2005, vol. 27, pp. 506-517.
Herr et al., *J. Urol.*, 163:60-62 (2000).
Izawa et al., *Clin. Cancer Res.*, 8:1258-1270 (2002).
Koshida, K. et al., "Prospects for Molecular Research in Urological Oncology: Bladder Cancer," *Acta Urol. Jpn.*, 2001, vol. 41, pp. 815-818, Translation of Abstract Only.
Kuball et al., *Journal of Clinical Oncology*, 20(4):957-965 (2002).
Lin, L-F. et al., "A System for the Enhancement of Adenovirus Mediated Gene Transfer to Uro-Epithelium," *The Journal of Urology*, Aug. 2002, vol. 168, pp. 813-818.
Luo, Y. et al., "Recombinant bacilli Calmette-Guérin (BCG) expressing human interferon-alpha 2B demonstrates enhanced immunogenicity," *Clin. Exp. Immunol.*, 2001, vol. 123, pp. 264-270.
Marshall, E., "Gene Therapy's Growing Pains," *Science*, 1955, vol. 269, pp. 1050-1055.
Miller, N. et al., "Targeted Vectors for Gene Therapy," *FASEB J.*, 1995, vol. 9, pp. 190-199.
Nagabhushan, T.L., et al. "Enhancement of intravesical delivery with Syn3 potentiates interferon-α2b gene therapy for superficial bladder cancer," *Cytokine & Growth Factor Reviews*, 2007, vol. 18, pp. 389-394.
O'Donnell et al., *J. Urol.*, 166:1300-1305 (2001).
Orkin et al., "Report and Recommendations of the Panel to Assess the NIH Investment in Research on Gene Therapy," issued by the U.S. National Institutes of Health, Dec. 1995.
Pagliaro et al., *J. Clin. Oncol.*, 21(12):2247-2253 (2003).
Papageorgiou, Angela, et al. "Role of Tumor Necrosis Factor-Related Apoptosis-Inducing Ligand in Interferon-Induced Apoptosis in Human Bladder Cancer Cells," Cancer Research, 2004, vol. 64, pp. 8973-8979.
Pouton, C.W. et al., "Key issues in non-viral gene delivery," *Advanced Drug Delivery Reviews*, 2001, vol. 46, pp. 187-203.
Read, M.L. et al., "Barriers to Gene Delivery Using Synthetic Vectors," Chapter 2 in *Advanced Genetics*, Elsevier, Inc., 2005, vol. 53, pp. 19-46.
Ross, G. et al., "Gene Therapy in the United States: A Five-Year Status Report," *Hum. Gene Ther.*, Sep. 1996, vol. 7, pp. 1781-1790.
Shiau, A-L. et al., "Postoperative immuno-gene therapy of murine bladder tumor by in vivo administration of retroviruses expressing mouse interferon-γ," *Cancer Gene Therapy*, 2001, vol. 8, No. 1, pp. 73-81.
Sutton, M.A. et al., "In Vivo Adenovirus-Mediated Suicide Gene Therapy of Orthotopic Bladder Cancer," *Molecular Therapy*, Sep. 2000, vol. 2, No. 3, pp. 211-217.
Tao, Z., "Efficacy of a single intravesical treatment with Ad-IFN/Syn 3 is dependent on dose and urine IFN concentration obtained: implications for clinical investigation," Cancer Gene Therapy, 2006, vol. 13, pp. 125-130.
Verma, I.M. et al., "Gene Therapy—Promised, Problems and Prospects," *Nature*, Sep. 1997, vol. 389, pp. 239-242.
Verma, I.M. et al., "Gene Therapy: Twenty-First Century Medicine," *Ann. Rev. Biochem.*, 2005, vol. 74, pp. 711-738.
Yamashita et al., *Cancer Gene Therapy*, 9:687-691 (2002).
Zhang, X., et al. "Adenoviral-mediated interferon α overcomes resistance to the interferon protein in various cancer types and has marked bystander effects," Cancer Gene Therapy, 2007, vol. 14, pp. 241-250.
Slaton, J.W. et al., "Interferon-α-mediated Down-Regulation of Angiogenesis-related Genes and Therapy of Bladder Cancer Are Dependent on Optimization of Biological Dose and Schedule," *Clinical Cancer Research*, Oct. 1999, vol. 5, pp. 2726-2734.

\* cited by examiner

METHODS AND COMPOSITIONS FOR TREATMENT OF INTERFERON-RESISTANT TUMORS

CROSS-REFERENCES TO RELATED APPLICATIONS

This application claims benefit of U.S. Provisional Application No. 60/528,525, filed Dec. 10, 2003, which application is incorporated herein by reference for all purposes.

BACKGROUND OF THE INVENTION

Interferon protein therapy is well established in the clinical environment as a treatment for a variety of cancers. Two widely used commercially available interferon species produced by recombinant DNA technology are interferon α-2b recombinant (Intron A®, Schering Corporation) and interferon α-2a recombinant (Roferon®, Hoffman LaRoche, Inc.). Intron A is indicated for use in the treatment of malignant melanoma in combination with surgery, aggressive follicular Non-Hodgkin's Lymphoma in combination with anthracycline chemotherapy, intralesional treatment of condylomata acuminata, hairy cell leukemia, and AIDS-Related Kaposi's Sarcoma. Roferon is indicated for use in the treatment of Philadelphia chromosome positive chronic myelogenous leukemia (CML) and AIDS-related Kaposi's sarcoma.

Additionally, investigational approaches to the use of recombinant vectors encoding interferon species have been evaluated for anti-tumor effects including the treatment of cancers of the ovary, kidney, and bladder, multiple myeloma, melanoma, certain lymphomas and leukemias, and Kaposi's sarcoma. The antitumor activities of replication deficient adenoviruses encoding interferon (Ad-IFNα) have been reported against a variety of human tumor xenografts following direct injection (Ahmed et. al., *Cancer Gene Therapy*, 8:788-95 (2001)), which included human transitional bladder carcinoma (TCC) xenografts (Izawa et al., *Clin. Cancer Res.*, 8:1258-1270 (2002)). These studies show that interferon can mediate both direct antitumor activity and a significant bystander effect, characterized by the activation of host effector cells, enhanced apoptosis, and the inhibition of angiogenesis.

One particularly notable application where recombinant interferon protein has been evaluated for efficacy is in the treatment of bladder cancer. Superficial bladder cancers are diagnosed in over 45,000 patients/year in the United States. The disease is typically characterized as a slowly progressing malignancy that originates from the surface lining of the urothelium. While most of these superficial cancers can be adequately managed with periodic transurethral resection (TUR) and surveillance, this is far from an optimal approach because 60 to 70 percent of superficial tumors recur after TUR, and up to 30 percent evolve into more aggressive, potentially lethal cancers. The high recurrence rate and the unpredictability of the progression patterns have led to the widespread use of intravesical therapy for local control of the disease. Immunotherapy with intravesically instilled *Bacillus* Calmette-Guerin (BCG) can usually delay disease progression in newly diagnosed patients. Unfortunately this therapy does not produce a qualitative change in the underlying biology of the tumor and many patients remain at substantial risk of eventual progressing to invasive, life-threatening cancer. In fact, even with close surveillance and follow-up, at least 50% of patients will eventually recur, and 30% will die of metastatic bladder cancer, despite originally presenting with "only" carcinoma in situ. Herr et al., *J. Urol.*, 163:60-61 (2000) and Dalbagni et al., *Urol. Clin. North Am.*, 27:137-146 (2000). Clearly, more effective intravesical therapies are necessary to improve overall survival and provide an alternative to radical cystectomy.

Intravesical interferon-α2b (IFNα2b) recombinant (Intron A) is well tolerated as a monotherapy in superficial bladder cancer patients and is an approved indication for this agent in many countries. Intron A has demonstrated dose-related clinical efficacy as a salvage therapy in the scenario of BCG failure, although the durability of the response is limited and most patients relapse within the first year of treatment. Belldegrun et al., *J. Urol.*, 159(6):1793-801 (1998). Recently, Intron A has been combined with BCG in an attempt to enhance the cellular immune response to BCG and improve the response to therapy. O'Donnell et al., *J. Urol.*, 166:1300-1304 (2001). Combination therapy has been effective in BCG refractory TCC, but many of these initial responders relapse with superficial disease and ultimately require cystectomy.

Gene therapy employing recombinant vectors encoding interferon species provides a promising alternate approach to the treatment of refractory superficial bladder cancer. Local delivery can maximize transgene expression in the urothelium and minimize vector distribution to vital organs outside of the bladder. In addition, efficient transfer of a gene encoding a secreted protein (e.g., IFNα2b) to both normal and malignant cells of the urothelium can generate a potent anti-tumor bystander effect coincident with sustained local protein concentrations in the urine.

SUMMARY OF THE INVENTION

The present invention provides methods for the treatment of interferon resistant tumors through the use of recombinant vectors encoding interferon species. In particular, it is noted that interferon species provided by recombinant vectors possess properties not associated with the available recombinantly produced interferon proteins. The present invention further provides compositions useful in the treatment of interferon resistant tumors using recombinant vectors encoding interferons.

DETAILED DESCRIPTION OF THE INVENTION AND PREFERRED EMBODIMENTS

Figure 1:
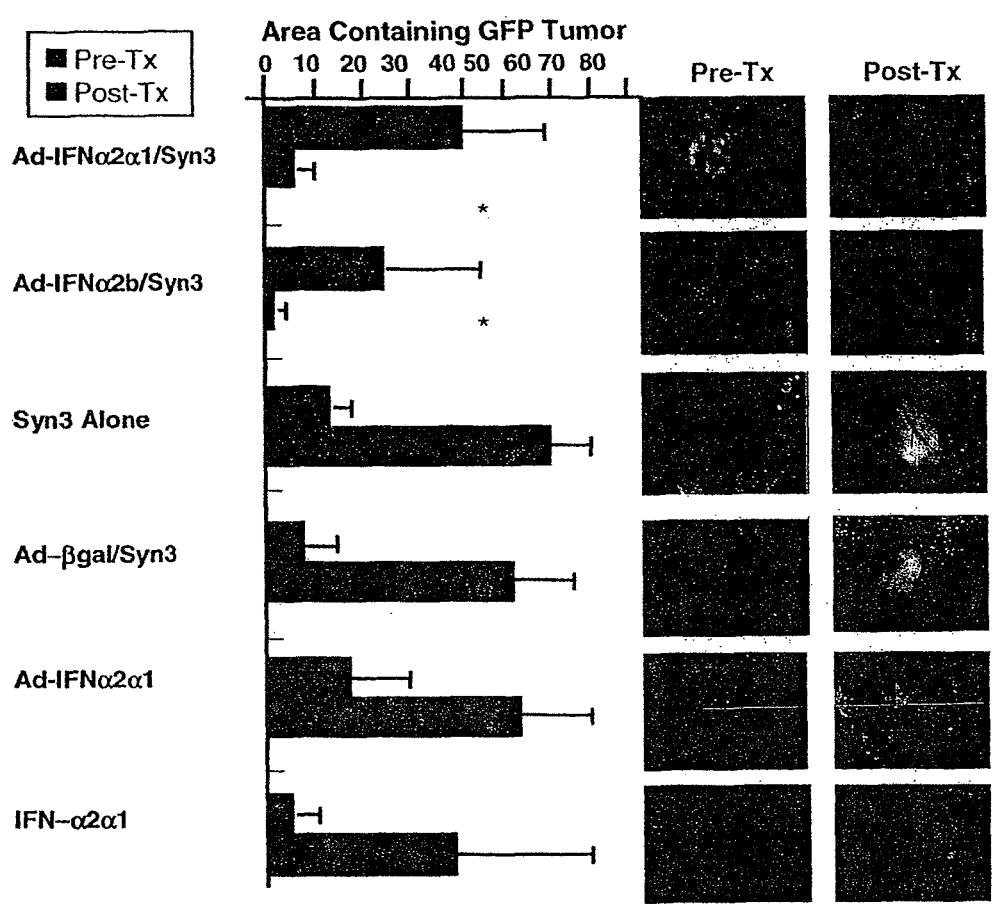
FIG. 1 provides a data of the effect of intravestical Ad-IFN-α2α1/Syn 3 or Ad-IFN-α2b/Syn3 on tumor regression. The graph at the left of the panel shows marked decrease in the pre-treatment tumor size 21 days after Ad-IFNα2α1/Syn 3 or Ad-IFNα2b/Syn3 treatment*, P=0.0024. All other treatment groups showed progressive tumor growth including Ad-IFNα2α1 without Syn3 or the IFN-α2α1 protein alone. To the right are a series of fluorescence micrographs providing a representative example of pre-treatment tumor images and those taken 21 days later from individual mice in each treatment group.

The present invention provides a method of treating an interferon-resistant tumor by contacting the tumor with a recombinant vector encoding an interferon such that the cells of the tumor transduced by the vector express the interferon encoded by the vector.

As used herein, the term "interferon-resistant tumor" refers to a tumor that is refractory to treatment by the administration of interferon protein in accordance with conventional interferon treatment protocols. In the case of bladder cancer, a tumor is considered refractory to interferon treatment if the tumor fails to diminish in a course of therapy of intravesical administration of up to six weekly administrations of approximately 100 million units of Intron A for an exposure time of approximately 1 hour. In the case of malignant melanoma, a tumor is considered to be refractory to interferon treatment if the tumor fails to respond following a treatment regimen comprising the intravenous administration of approximately 20 MIU/m$^2$ of Intron A for 5 consecutive days per week for 4 weeks (induction phase) following by a maintenance phase of 3 times per week for up to 48 weeks at a dose of approximately 10 MIU/m$^2$. In the case of diffuse diseases such as lymphomas and leukemias, there is not generally a localized tumor mass, but rather a systemic disease characterized by neoplastic white blood cells. For purposes of the present invention, neoplastically transformed cells shall be considered tumors. In the case of follicular lymphomas, the tumor is considered refractory to interferon treatment if the individual fails to respond to a treatment regimen comprising subcutaneous administration of 5 MIU of Intron A three times per week for up to 18 months. In the case of Ph-positive chronic myologenous leukemia (CML), the tumor is considered refractory to treatment if the individual fails to respond to a treatment regimen consisting of a daily intramuscular or subcutaneous injection of approximately 9 MIU of Roferon for a treatment period of up to 5 to but as long as 18 months. Alternative to clinical evaluation and response to conventional interferon protein therapy, tumors may be identified as being refractory to administration of interferon protein as determined in vitro in accordance with conventional in vitro assay procedures. Characterization of a tumor as an interferon-resistant tumor may be determined by exposure of the interferon-resistant tumor cells comprising the tumor being resistant to growth inhibition by contact with at least 100,000 units of Intron A protein as determined in substantial accordance with the MTT assay described in Example 6 herein.

The term "tumor" refers to a collection of neoplastic cells. The term "neoplastic cell" refers to a cell displaying an aberrant growth phenotype characterized by independence of normal cellular growth controls. As neoplastic cells are not necessarily replicating at any given time point, the term neoplastic cells comprise cells which may be actively replicating or in a temporary nonreplicative resting state (G1 or G0). Localized populations of neoplastic cells are referred to as neoplasms or tumors (these terms are considered interchangeable). As previously noted, the term tumors as used herein may also refer to diffuse neoplastic diseases such as leukemia where no substantial localized tumor mass is present. Neoplasms or tumors may be malignant or benign. Malignant tumors are also referred to as cancers. In preferred embodiments, the cancer is an epithelial tumor, e.g., breast, lung, prostate, colorectal, kidney, stomach, bladder or ovarian, or any cancer of the gastrointestinal tract.

While most tumors are generally monoclonal in origin, a tumor originating from a monoclonal source may differentiate over time. Consequently, a tumor (including diffuse tumors) may possess individual cells or cell subpopulations which are interferon-resistant and cells or cell subpopulations that are sensitive to interferon treatment. The term interferon-resistant tumors refers to tumors where a substantial population (i.e., at least 20%) of the cells which comprise the tumors are interferon-resistant as determined in accordance with the MTT assay described in Example 6 herein.

The term "treatment," as used herein, is intended to refer to the introduction of nucleic acid encoding an interferon to a patient for the purpose of exposing a tissue of interest comprising neoplastic cells to interferon. Thus, for example, a "cancerous" tissue is intended to refer to a tissue in which one or more cells is classified as cancerous, malignant, tumorous, precancerous, transformed, or as an adenoma or carcinoma, or any other synonym commonly used in the art for these conditions. A treatment may be considered therapeutic if the treatment indicates an improvement in the physiological or psychological condition of the subject in which the neoplasm is present. Improvement in the condition may be measured by a variety of means including reduced tumor burden, reduction of tumor progression, slowing of tumor progression, increased survival, tumor regression, amelioration symptoms associated with tumor burden including but not limited to fatigue, anorexia, pain, depression, neutropenia and cognitive dysfunction.

As used herein, the term "interferon" (abbreviated "IFN") refers collectively to type 1 and type 2 interferons including deletion, insertion, or substitution variants thereof, biologically active fragments, and allelic forms. As used herein, the term interferon (abbreviated "IFN") refers collectively to type 1 and type 2 interferons. Type 1 interferon includes interferons-$\alpha$, -$\beta$ and -$\omega$ and their subtypes. Human interferon-$\alpha$ has at least 14 identified subtypes while interferon-$\beta$ has 3 identified subtypes. Particularly, preferred interferon-alphas include human interferon alpha subtypes including, but not limited to, $\alpha$-1 (GenBank Accession Number NP 076918), $\alpha$-1b (GenBank Accession Number AAL35223), $\alpha$-2, $\alpha$-2a (GenBank Accession Number NP000596), $\alpha$-2b (GenBank Accession Number AAP20099), $\alpha$-4 (GenBank Accession Number NP066546), $\alpha$-4-b (GenBank Accession Number CAA26701), $\alpha$-5 (GenBank Accession Numbers NP 002160 and CAA26702), $\alpha$-6 (GenBank Accession Number CAA26704), $\alpha$-7 (GenBank Accession Numbers NP 066401 and CAA 26706), $\alpha$-8 (GenBank Accession Numbers NP002161 and CAA 26903), $\alpha$-10 (GenBank Accession Number NP 002162), $\alpha$-13 (GenBank Accession Numbers NP 008831 and CAA 53538), $\alpha$-14 (GenBank Accession Numbers NP 002163 and CAA 26705), $\alpha$-16 (GenBank Accession Numbers NP 002164 and CAA 26703), $\alpha$-17 (GenBank Accession Number NP 067091), $\alpha$-21 (GenBank Accession Numbers P01568 and NP002166), and consensus interferons as described in Stabinsky, U.S. Pat. No. 5,541,293, issued Jul. 30, 1996, Stabinsky, U.S. Pat. No. 4,897,471, issued Jan. 30, 1990, and Stabinsky, U.S. Pat. No. 4,695,629, issued Sep. 22, 1987, the teachings of which are herein incorporated by reference, and hybrid interferons as described in Goeddel et al., U.S. Pat. No. 4,414,150, issued Nov. 8, 1983, the teachings of which are herein incorporated by reference. Type 2 interferons are referred to as interferon $\gamma$ (EP 77,670A and EP 146,354A) and subtypes. Human interferon gamma has at least 5 identified subtypes, including interferon omega 1 (GenBank Accession Number NP 002168). Construction of DNA sequences encoding inteferons for expression may be accomplished by conventional recombinant DNA techniques based on the well-known amino acid sequences referenced above and as described in Goeddel et al., U.S. Pat. No. 6,482,613, issued Nov. 19, 2002, the teachings of which are herein incorporated by reference.

"Biologically active" fragments of interferons may be identified as having any anti-tumor or anti-proliferative activity as measured by techniques well known in the art (see, for example, Openakker et al., supra; Mossman, *J. Immunol. Methods*, 65:55 (1983) and activate IFN responsive genes through IFN receptor mediated mechanisms. Soluble IFN-$\alpha$ and IFN-$\beta$ proteins are generally identified as associating with the Type 1 IFN receptor complex (GenBank Accession Number NP 000865) and activate similar intracellular signaling pathways. IFN-$\gamma$ is generally identified as associating with the type II IFN receptor. Ligand-induced association of both types of IFN receptors results in the phosphorylation of the receptors by Janus kinases subsequently activating STATs (signal transducers and activators of transcription) proteins and additional phosphorylation events that lead to the formation of IFN-inducible transcription factors that bind to IFN response elements presented in IFN-inducible genes. Polypeptides identified as activating the IFN pathways following association with Type 1 and/or Type 2 IFN receptors are considered interferons for purposes of the present invention.

The term "recombinant vector" refers to viral and nonviral vectors comprising an interferon expression cassette that has been prepared using conventional recombinant DNA technology. The term "interferon expression cassette" is used herein to define a nucleotide sequence containing regulatory elements operably linked to the interferon coding sequence so as to result in the transcription and translation of an interferon in a cell. The term "regulatory element" refers to promoters, enhancers, transcription terminators, polyadenylation sites, and the like. The expression cassette may also contain other sequences aiding expression and/or secretion of the interferon gene. The regulatory elements may be arranged so as to allow, enhance or facilitate expression of the interferon only in a particular cell type. For example, the expression cassette may be designed so that the interferon is under control of an inducible promoter, tissue specific or tumor specific promoter, or temporal promoter. In general, the interferon is provided in an expression vector comprising the following elements linked sequentially at appropriate distances for functional expression: a promoter, an initiation site for transcription, a 3' untranslated region, a 5' mRNA leader sequence, a nucleic acid sequence encoding an interferon polypeptide, and a polyadenylation signal.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked, but not directly flanked and may even function in trans from a different allele or chromosome.

The term "inducible promoter" refers to promoters that facilitate transcription of the interferon transgene preferably (or solely) under certain conditions and/or in response to external chemical or other stimuli. Examples of inducible promoters are known in the scientific literature (see, e.g., Yoshida et al., *Biochem. Biophys. Res. Comm.*, 230:426-430 (1997); Iida et al., *J. Virol.*, 70(9):6054-6059 (1996); Hwang et al., *J. Virol.*, 71(9):7128-7131 (1997); Lee et al., *Mol. Cell. Biol.*, 17(9):5097-5105 (1997); and Dreher et al., *J. Biol. Chem.*, 272(46):29364-29371 (1997). Examples of radiation inducible promoters include the EGR-1 promoter. Boothman et al., volume 138, supplement pages S68-S71 (1994).

Tissue specific and tumor specific promoters are well known in the art and include promoters active preferentially in smooth muscle (α-actin promoter), pancreas specific (Palmiter et al., *Cell*, 50:435 (1987)), liver specific (Rovet et al., *J. Biol. Chem.*, 267:20765 (1992); Lemaigne et al., *J. Biol. Chem.*, 268:19896 (1993); Nitsch et al., *Mol. Cell. Biol.*, 13:4494 (1993)), stomach specific (Kovarik et al., *J. Biol. Chem.*, 268:9917 (1993)), pituitary specific (Rhodes et al., *Genes Dev.*, 7:913 (1993)), prostate specific (Henderson et. al., U.S. Pat. No. 5,698,443, issued Dec. 16, 1997), etc.

The term "temporal promoters" refers to promoters that drive transcription of the interferon transgene at a point later in the viral cycle relative to the promoter controlling expression of the response element and are used in conjunction with viral vector systems. Examples of such temporally regulated promoters include the adenovirus major late promoter (MLP), and other late promoters. For herpes simplex viruses, an example of temporal promoter includes the latent activated promoters.

The term "nonviral vector" refers to an autonomously replicating, extrachromosomal circular DNA molecules, distinct from the normal genome and nonessential for cell survival under nonselective conditions capable of effecting the expression of an interferon coding sequence in the target cell. Plasmids autonomously replicate in bacteria to facilitate bacterial production, but it is not necessary that such plasmids containing the interferon coding sequence replicate in the target cell in order to achieve the therapeutic effect. Additional genes, such as those encoding drug resistance, can be included to allow selection or screening for the presence of the recombinant vector. Such additional genes can include, for example, genes encoding neomycin resistance, multi-drug resistance, thymidine kinase, β-galactosidase, dihydrofolate reductase (DHFR), and chloramphenicol acetyl transferase.

In order to facilitate delivery of the interferon gene to a particular tissue or organ, it may be advantageous to incorporate elements into the nonviral delivery system which facilitate cellular targeting. For example, a lipid encapsulated expression plasmid may incorporate modified surface cell receptor ligands to facilitate targeting. Although a simple liposome formulation may be administered, the liposomes either filled or decorated with a desired composition of the invention can delivered systemically, or can be directed to a tissue of interest, where the liposomes then deliver the selected therapeutic/immunogenic peptide compositions. Examples of such ligands include antibodies, monoclonal antibodies, humanized antibodies, single chain antibodies, chimeric antibodies or functional fragments (Fv, Fab, Fab') thereof. Alternatively, nonviral vectors can be linked through a polylysine moiety to a targeting moiety as described in Wu et al. U.S. Pat. No. 5,166,320, issued Nov. 24, 1992, and Wu et al., U.S. Pat. No. 5,635,383, issued Jun. 3, 1997, the teachings of which are herein incorporated by reference.

The terms "viral vector" and "virus" are used interchangeably herein to refer to any of the obligate intracellular parasites having no protein-synthesizing or energy-generating mechanism. The viral genome may be RNA or DNA contained with a coated structure of protein of a lipid membrane. The terms virus(es) and viral vector(s) are used interchangeably herein. The viruses useful in the practice of the present invention include recombinantly modified enveloped or nonenveloped DNA and RNA viruses, preferably selected from baculoviridiae, parvoviridiae, picornoviridiae, herpesviridiae, poxyiridae, or adenoviridiae. The viruses may be naturally occurring viruses or their viral genomes may be modified by recombinant DNA techniques to include expression of exogenous transgenes and may be engineered to be replication deficient, conditionally replicating or replication competent. Chimeric viral vectors which exploit advantageous elements of each of the parent vector properties (see, e.g., Feng, et al., *Nature Biotechnology*, 15:866-870 (1997)) may also be useful in the practice of the present invention. Minimal vector systems in which the viral backbone contains only the sequences need for packaging of the viral vector and may optionally include a transgene expression cassette may also be produced according to the practice of the present invention. Although it is generally favored to employ a virus from the species to be treated, in some instances, it may be advantageous to use vectors derived from different species that possess favorable pathogenic features. For example, equine herpes virus vectors for human gene therapy are described in PCT International Publication No. WO98/27216, published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in PCT International Publication No. WO 97/06826, published Apr. 10, 1997.

The term "replication deficient" refers to vectors that are highly attenuated for replication in a wild type mammalian cell. In order to produce such vectors in quantity, a producer cell line is generally created by co-transfection with a helper virus or genomically modified to complement the missing functions. For example, HEK293 cells have been engineered to complement adenoviral E1 deletions allowing propagation of the E1 deleted replication deficient adenoviral vectors in 293 cells. The term "replication competent viral vectors" refers to a viral vector that is capable of infection, DNA replication, packaging and lysis of an infected cell. The term "conditionally replicating viral vectors" is used herein to refer to replication competent vectors that are designed to achieve selective expression in particular cell types. Such conditional replication may be achieved by operably linking tissue specific, tumor specific or cell type specific or other selectively induced regulatory control sequences to early genes (e.g., the E1 gene of adenoviral vectors).

Cell type specificity or cell type targeting may also be achieved in viral vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham et al., *J. Virol.*, 71(11):8221-8229 (1997) (incorporation of RGD peptides into adenoviral fiber proteins); Amberg et al., *Virology*, 227:239-244 (1997) (modification of adenoviral fiber genes to achieve tropism to the eye and genital tract); Harris et al., *TIG*, 1200:400-405 (1996); Stevenson et al., *J. Virol.*, 71(6):4782-4790 (1997); Michael et al., *Gene Therapy*, 2:660-668 (1995) (incorporation of gastrin releasing peptide fragment into adenovirus fiber protein); and Ohno et al., *Nature Biotechnology*, 15:763-767 (1997) (incorporation of Protein A-IgG binding domain into Sindbis virus). Other methods of cell specific targeting have been achieved by the conjugation of antibodies or antibody fragments to the envelope proteins (see, e.g., Michael et al., *J. Biol. Chem.*, 268:6866-6869 (1993), Watkins et al., *Gene Therapy*, 4:1004-1012 (1997); Douglas et al., Nature Biotechnology, 14:1574-1578 (1996). Alternatively, particular moieties may be conjugated to the viral surface to achieve targeting (see, e.g., Nilson et al., *Gene Therapy*, 3:280-286 (1996) (conjugation of EGF to retroviral proteins). Targeting of vectors may also be achieved in accordance with the teaching of Murphy, U.S. Pat. No. 6,635,476, issued Oct. 21, 2003, the teachings of which are herein incorporated by reference. These targeting modifications may be introduced into the viral vectors of the present invention in addition to or in combination with other modifications to the viral genome. Targeting modifications may be used with replication deficient, replication competent or conditionally replicating viruses.

Alternatively, cell type targeting with viral vectors may be achieved through the use of a pathway responsive promoter driving a repressor of viral replication. The term "pathway-responsive promoter" refers to DNA sequences that bind a certain protein and cause nearby genes to respond transcriptionally to the binding of the protein in normal cells. Such promoters may be generated by incorporating response elements which are sequences to which transcription factors bind. Such responses are generally inductive, though there are several cases where increasing protein levels decrease transcription. Pathway-responsive promoters may be naturally occurring or synthetic. Pathway-responsive promoters are typically constructed in reference to the pathway of a functional protein which is targeted. For example, a naturally occurring p53 pathway-responsive promoter would include transcriptional control elements activated by the presence of functional p53 such as the p21 or bax promoter. Alternatively, synthetic promoters containing p53 binding sites upstream of a minimal promoter (e.g., the SV40 TATA box region) may be employed to create a synthetic pathway-responsive promoter. Synthetic pathway-responsive promoters are generally constructed from one or more copies of a sequence that matches a consensus binding motif. Such consensus DNA binding motifs can readily be determined. Such consensus sequences are generally arranged as a direct or head-to-tail repeat separated by a few base pairs. Elements that include head-to-head repeats are termed palindromes or inverted repeats and those with tail-to-tail repeats are termed everted repeats.

In the preferred practice of the invention, the viral vector is an adenovirus. The term "adenovirus" is synonymous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F sugenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes, but is not limited to, bovine adenovirus types 1, 2, 3, 4, 7, and 10. The term canine adenoviruses includes, but is not limited to, canine types 1 (strains CLL, Glaxo, RI261, Utrect, Toronto 26-61) and 2. The term equine adenoviruses includes, but is not limited to, equine types 1 and 2. The term porcine adenoviruses includes, but is not limited to, porcine types 3 and 4.

The term viral vector includes replication deficient, replication competent, and conditionally replicating viral vectors.

More preferred are vectors derived from human adenovirus types 2 and 5. These vectors may incorporate particular modifications to enhance their therapeutic potential. For example, they may include deletions of E1a and E1b genes. Certain other regions may be enhanced or deleted to provide specific features. For example, upregulation of the E3 region is described to reduce the immunogenicity associated with human adenoviral vectors administered to human subjects. The E4 region has been implicated as important to expression of transgenes from the CMV promoter, however the E4orf 6 protein has been described as leading to the degradation of p53 in target cells in the presence of E1b large protein. Steegenga et al., *Oncogene*, 16:345-347 (1998). Consequently, the elimination of such sequences of adenoviral vectors is preferred.

In one embodiment of the invention when using replication competent vectors to deliver the interferon gene, it is preferred that an adenoviral vector be employed containing specific deletions in the E1A region so as to reduce the ability of the E1a gene product to bind to the p300 and Rb proteins while retaining the transactivating function of the E1a CR3 domain. The vectors of the present invention contain deletions in the E1a coding sequence to eliminate p300 and p105-Rb binding sites in the 13S coding sequence. In one preferred embodiment of the invention, the p300 binding deletions are represented by deletions of amino acids from about 4 to about 25 or from about 36 to about 49. In one preferred embodiment of the invention, the Rb binding deletions are represented by elimination of amino acids from about 111-127, preferably from about 111-123. More preferred is a vector wherein the deletion in the E1a-p300 binding domain comprises a deletion of the codons for amino acids 4 to 25 of the adenoviral E1a gene product. More preferred is a vector wherein deletion in the E1a-Rb binding domain comprises a deletion of the codons for amino acids 111-123 of the adenoviral E1a gene product. Alternatively, pRb binding may be eliminated by the introduction of a mutation to eliminate amino acids 124-127 of the E1A 289R and 243R proteins. In the most preferred embodiment of the present invention as exemplified herein the vector comprises a deletion of amino acids 4-25 and 111-123 of the E1a 13S gene product.

Additionally, the elimination of amino acids from approximately 219 to 289 of the E1a 289R protein and 173 to 243 of the E1A 243R protein may be introduced. For example, by introducing a point mutation at a position corresponding to position 1131 of the human Ad5 genome (i.e., changing the cytosine$^{1131}$ to a guanine) creates a stop codon. This mutation results in the elimination of amino acids 219 to 289 of the E1a 289R protein and 173 to 243 of the E1A 243R protein. This mutation is made optionally in addition to the deletions in Rb and p300 binding described above.

The practice of the present invention involves "contacting" the tumor with a recombinant vector encoding interferon. Contact of the tumor cells is accomplished by exposure of the tumor cells with the recombinant vector such that the cells of the tumor are transduced by the vector expressing the interferon encoded by the vector. The particular means by which the tumor is contacted by the vector will differ depending on the nature of the tumor to which the vector is being delivered. In some embodiments of the invention, the compositions of the invention can be administered directly into a tissue by injection or into a blood vessel supplying the tissue of interest. In further embodiments of the invention, where local administration is preferred, but where it is difficult to gain physical access to the tumor site, the compositions are administered through catheters or other devices to allow access to a remote tissue of interest, such as an internal organ. The compositions of the invention can also be administered in depot type devices, pumps, implants, or formulations to allow slow or sustained release of the compositions. In further embodiments of the invention, the compositions of the invention are administered "locoregionally", i.e., intravesically, intralesionally, and/or topically. In other embodiments of the invention, particularly when treating diffuse tumors (such as leukemias) or metastatic disease, the compositions of the invention may be administered systemically by intravenous or intraarterial routes of administration.

In order to demonstrate the performance of the present invention, recombinant vectors derived from human adenovirus type 5 were used to encode interferon species. Two adenovirus vectors containing IFN$\alpha$ genes were evaluated in these studies. One vector contained the human interferon $\alpha$2b gene (Ad-IFN$\alpha$2b), and the other contained a chimeric human "hybrid" interferon gene comprised of the human $\alpha$2 N-terminus joined to the human $\alpha$1C-terminus (Ad-IFN$\alpha$2$\alpha$1). Whereas IFN activity is generally species restricted, the hybrid interferon (aka 'universal' or IFN A/D) is active on cells derived from a variety of mammalian species including mouse and human. These two interferon vectors permitted evaluation of the effect of recombinant IFN$\alpha$ vectors on human tumors and the broader effects of the hybrid interferon that can elicit responses in both the cells of the murine and xenograft cells of the human tumor present in the mouse model.

To evaluate the response to intravestical IFN gene and protein therapy, an orthotopic bladder tumor model in nude mice was used. The model is described in Watanabe et al., Cancer Gene Therapy, 7:1575-1580 (2000) and Thou et al., Cancer Gene Therapy, 9:681-686 (2002). The amount of tumor found in histological sections of the bladders taken 21 days after treatment was highly correlative of the tumor burden calculated by imaging. Prior to intravesical treatment, the tumor burden of KU7 cells within the bladder of each mouse was imaged and quantitated two weeks after the cancer cells were instilled in accordance with the teaching of Watanabe et al. For intravesical instillation, the vectors were administered in conjunction with Syn3 (Example 1). The mice then received various intravesical treatment for one hour on two consecutive days as described in the Examples herein. Three weeks later the bladders were imaged again for changes in tumor burden. As shown in FIG. 1 of the attached drawings, when either Ad-IFN$\alpha$2$\alpha$1/Syn3 or Ad-IFN$\alpha$2b/Syn3 was used, a marked tumor regression was observed (P<0.0024). In contrast, tumors grew rapidly following treatment with the control Ad-$\beta$gal/Syn3, Ad-IFN$\alpha$2$\alpha$1, or Syn3 alone. These results indicate that Syn3 markedly enhanced the efficacy of adenoviral vectors encoding IFN$\alpha$.

Because intravesical IFN$\alpha$ protein is used in clinical trials for superficial bladder cancer alone or in combination with BCG, experiments were conducted to further delineate differences in activity of Ad-IFN versus the interferon protein therapy. The efficacy of the hybrid interferon protein was compared to Ad-IFN$\alpha$2$\alpha$1 in the orthotopic tumor model described above. When 200,000 units (2 MIU/ml) of IFN$\alpha$2$\alpha$1 protein was given intravesically for 1 hour on 2 consecutive days, no significant tumor regression was noted. No antitumor effects were detected either when IFN$\alpha$2$\alpha$1 protein was instilled on days 1, 7 and 14 and evaluated for tumor burden 21 days after the first treatment. These results are in contrast to the effect observed following Ad-IFNa2a1/Syn3 therapy as demonstrated in FIG. 1. The urothelium appeared similar in all treatment groups including a mild degree of hyperplasia which was related to the initial trypsinization of the urothelium required to promote initial tumor cell adhesion.

Figure 2:
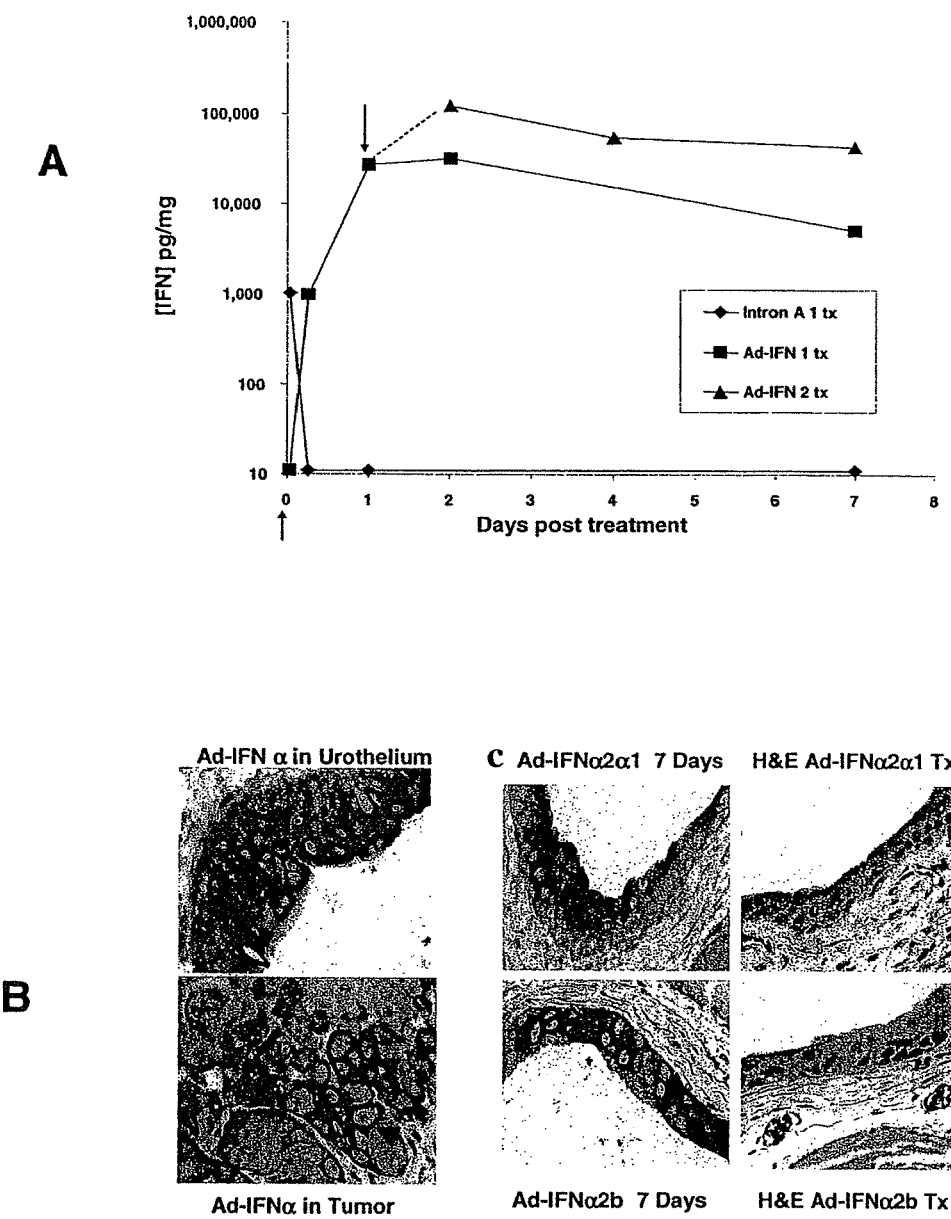
FIG. 2 provides a demonstration of prolonged IFN expression following Ad-IFN/Syn3 intravesical treatment. Panel A demonstrates that sustained levels of IFN are seen in the bladder homogenates of athymic mice treated once with Ad-IFNα2b/Syn3 which was increased after two exposures. In contrast, similar treatment with 200,000 IU of Intron A protein itself did not show any such high or prolonged IFN levels. Arrows indicate when treatment 1 and 2 were given. Panel B provides data indicating that the same high levels of IFN in the urothelium and adjacent bladder tumor is seen by immunohistochemical analysis 2 days after two treatments with Ad-IFNα2α1/Syn 3 in athymic mice. Arrows show strong perinuclear IFN staining present in many cells. Panel C demonstrates that similar high levels of IFN are seen in the urothelium of outbred Balb-C mice 7 days after treatment with either Ad-IFNα2α1/Syn 3 or Ad-IFNα2b/Syn3. No morphological changes in the urothelium were seen by histological examination or H&E stained sections.

In order to evaluated the level and duration of interferon expression following intravesical AdIFN$\alpha$/Syn3, a series of experiments were conducted using nontumor-bearing athymic mice with the same concentrations of Ad-IFN$\alpha$2b/Syn3 utilized for the foregoing efficacy studies, and compared a single intravesical treatment to two consecutive days of exposure for one hour. The IFN protein in the bladder tissue was assessed by harvesting the mouse bladders at various times after treatment and assaying for IFN protein present in tissue homogenates using an ELISA assay. One day after treatment, bladders contained approximately 50,000 pg/mg of Intron A, which slowly decreased to 5,000-10,000 pg/mg by 7d as shown in FIG. 2, Panel A of the attached drawings. In mice receiving a second Ad-IFN$\alpha$2b/Syn3 treatment, tissue concentrations reached 100,000 pg/mg and remained higher over a 7d period compared to the single exposure. In contrast, when 200,000 IU of IFN protein was instilled, IFN concentrations measured in tissue homogenates one hour after treatment were <1000 pg/mg, and no IFN protein was detected at later times. High concentrations of IFN protein were found in the majority of urothelial cells by immunohistochemical analysis 2 days after either Ad-IFN$\alpha$2$\alpha$1/Syn3 or Ad-IFN$\alpha$2b/Syn3 treatment (FIG. 2, Panel B). Similar staining was seen in many of the adjacent human tumor cells (FIG. 2, Panel B). In outbred Balb/C mice, strong IFN staining could also be seen in many of the urothelial cells five days after treatment on two consecutive days with either Ad-IFN$\alpha$2$\alpha$1/Syn3 or Ad-IFN$\alpha$2b/Syn3 (FIG. 2, Panel C). In addition, the bladder appeared to show little evidence of local toxicity upon histological examination (FIG. 2, Panel C). This is particularly important in the mice treated with Ad-IFN$\alpha$2$\alpha$1/Syn3 since the hybrid IFN is active in mouse cells.

Figure 3:
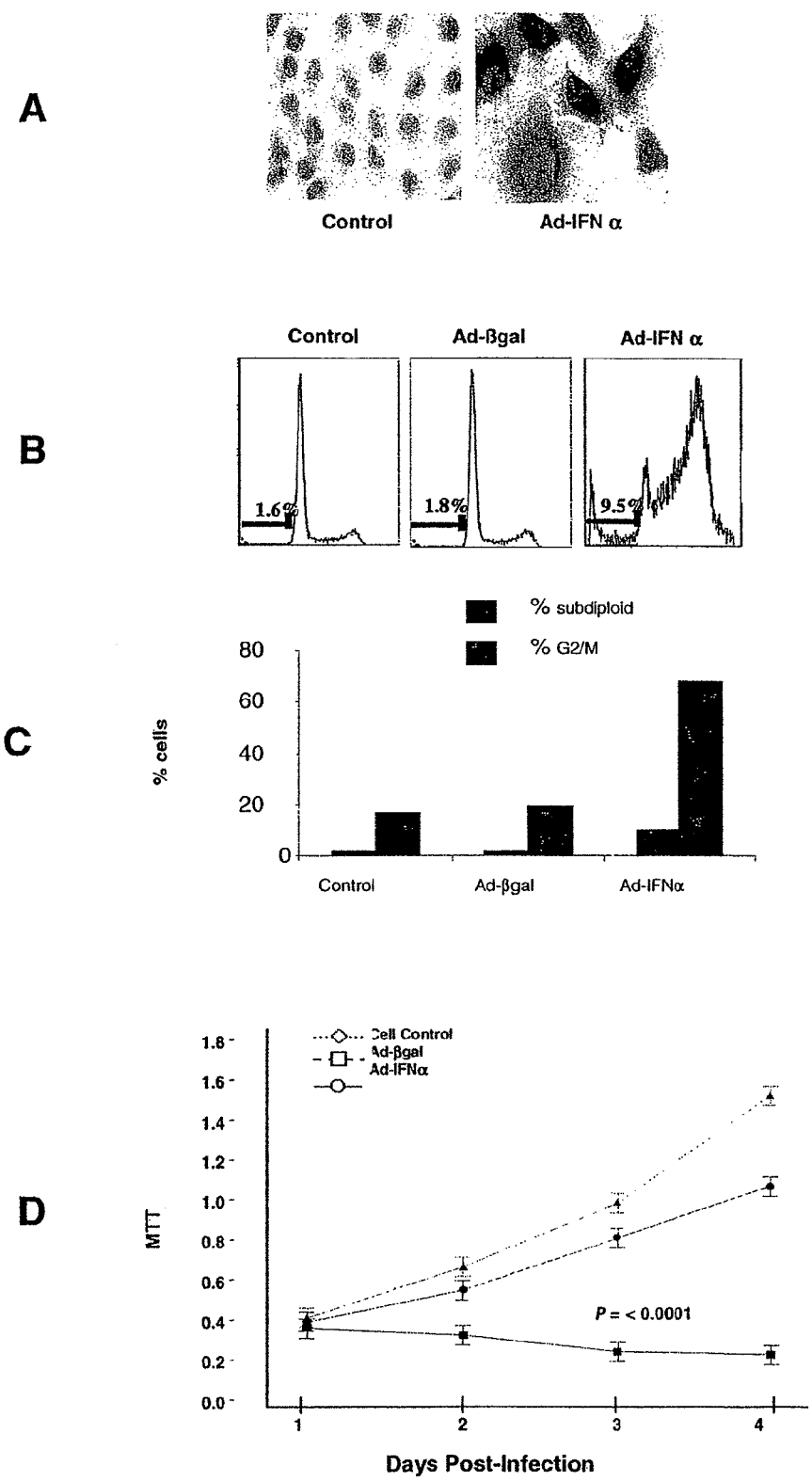
FIG. 3 provides a comparison of Ad-IFN cytotoxicity to bladder cancer cell lines resistant to over 100,000 IU of Intron A. Panel A shows the negative IFN staining in control cells (10× Magnification) and marked perinuclear IFN staining in 253J-BV cells treated with Ad-IFNα2α1 (40× Magnification). Panel B is data from a flow cytometric analysis showing increase in the number of subdiploid cells at 48 hrs after treatment of a 50 MOI Ad-IFNα2α1 in 253J B-V cells. Red bars indicate the subdiploid population. Panel C illustrates an increase in the number of G2/M cells following Ad-IFNα2α1 treatment to over 60% was observed. Panel D demonstrates the marked cytotoxicity to Ad-IFNα2α seen in the 253J B-V cells at the same 50 MOI of Ad-IFNα2α1. A 50 MOI of Ad-βgal was also used for these studies as a control and no cytotoxicity was seen, nor were changes observed in these cells when treated with 100,000 IU of Intron A. Similar results were observed using KU7 cells or using Ad-IFN-α2b.

In order to more fully illustrate the effect of vectors encoding interferon in the treatment of interferon resistant tumors, a series of experiments were conducted to evaluate vectors encoding interferon in interferon resistant tumor cell lines. Some human bladder cancer cell lines are resistant to interferon induced cell death even after exposure to more than 100,000 IU/ml of either IFN$\alpha$t or IFN$\alpha$ proteins in vitro in accordance with the MTT assay described herein. Certain cell interferon resistant tumor cell lines include the KU7 cells (which were used in the foregoing efficacy studies) and 253J B-V cells. When exposed to recombinant vectors encoding interferon, these interferon resistant tumor cell lines demonstrated sensitivity to Ad-IFN$\alpha$; treatment. For example, transduction of KU7 or 253J-BV cells with a 50 MOI of Ad-IFN-$\alpha$2$\alpha$1 or Ad-IFN-$\alpha$2b resulted in elevated IFN$\alpha$ expression in approximately 50% of cells as determined by immunocytochemical staining for IFN protein. A strong perinuclear IFN staining was often seen (FIG. 3, Panel A) accompanied by morphological changes such as an increase in size and a marked decrease in the number of mitosis. This resulted in significant cell cycle arrest at $G_2$/M (FIG. 3, Panels B and C), DNA fragmentation characteristic of apoptosis (FIG. 3, Panels B and C), and cytostasis (FIG. 3, Panel D).

Figure 4:
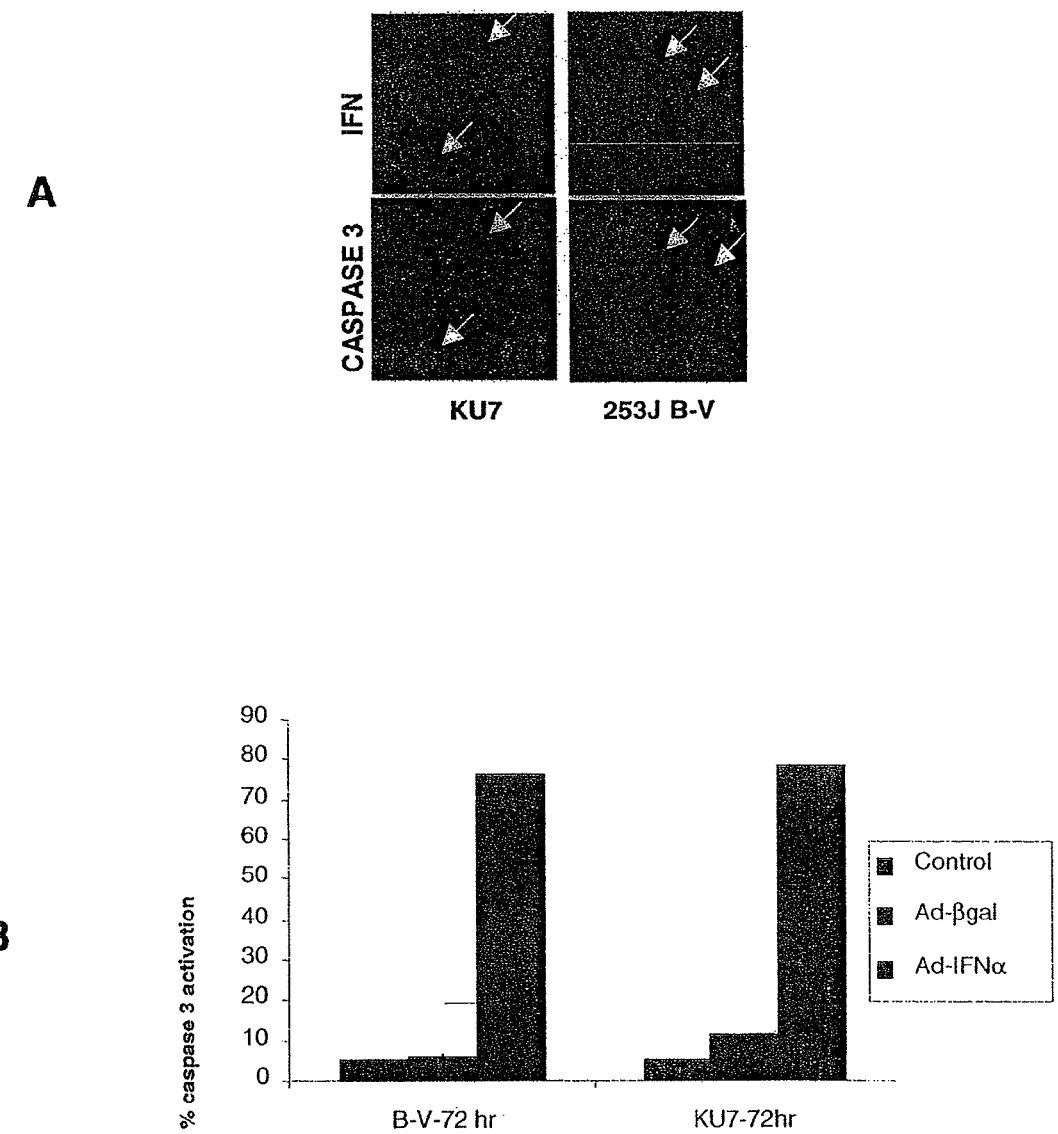
FIG. 4 illustrates caspase dependent cell death occurs in bladder cancer cells resistant to IFN protein following Ad-IFN treatment including cells which show no IFN staining. Panel A provides KU7 or 253J-BV cells treated with Ad-IFN-α2α1. Two by two optical channels merged images of triple staining of cells for IFN (red) and DNA (blue) upper panels and for active caspase-3 (green) and DNA (blue) lower panels are shown 36 h after treatment. Caspase activation and nuclear condensation is seen in cells expressing IFN (white arrows). Caspase activation, however, is also seen in IFN-nonexpressing cells found in close proximity of IFN-expressing cells (yellow arrows), demonstrating a bystander effect of IFN expression in the two different cellular populations. Panel B provides quantitation of caspase-3 activation in BV and KU7 cells 72 hr after Ad-IFN treatment at the same MOI.

To more fully elucidate the mechanism or mechanisms underlying the induction of cell death of these interferon resistant tumor cell lines following exposure to Ad-IFN, the effects of Ad-IFN$\alpha$ on caspase-3 activation as an independent marker for apoptosis. Transduction with Ad-IFNα stimulated marked activation of caspase-3 in both cell lines (FIG. 4, Panels A and B). Caspase-3 staining was seen in cells exhibiting a high level of IFN-α expression as well as in many adjacent cells that showed no evidence of IFN-α expression (FIG. 4a). Furthermore, when the percentage of caspase-3 positive cells was quantitated in both 253J-BV and KU7 cell lines 72 hr after Ad-IFN treatment at the same 50 MOI, over 70% of the cells were caspase-3 positive (FIG. 4, Panel B). Exposure to Ad-IFNα resulted in substantial cytotoxicity, since no population of the cells regrew when cultured over extended periods. These results were similar in bladder cancer cell lines evaluated, including all cell lines resistant to the IFNα protein. No such changes were seen in these cells following treatment with up to 100,000 IU/ml of the IFNα protein or Ad-βgal at a similar MOI. Since no more than 50% of the cells are transduced at this MOI, this also provided additional evidence to support a strong Ad-IFN induced bystander effect.

Figure 5:
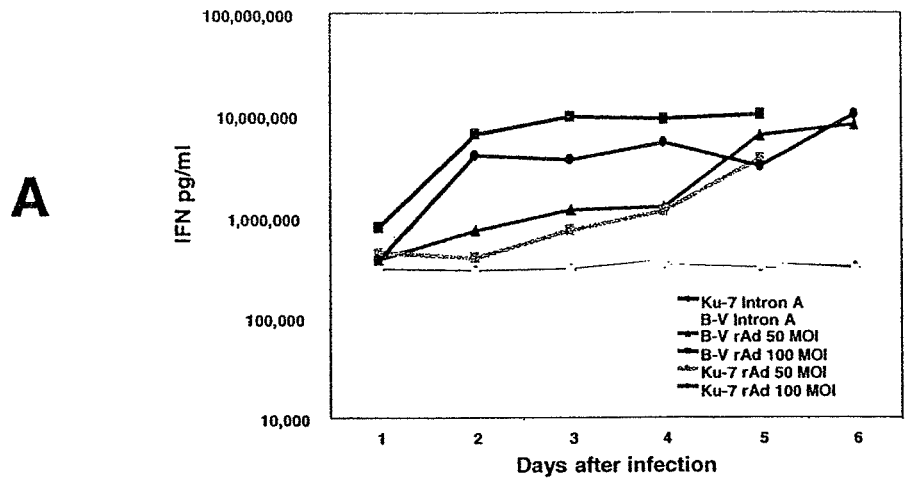
FIG. 5 is a comparison of Ad-IFN and Intron A on bladder cancer cells. Panel A illustrates the high and sustained production of IFN in the supernatant from B-V and KU7 following Ad-IFN treatment at two MOIs. Levels reached 10 million pg/ml (~2.5 million IU of IFN) in both cell lines. The addition of 400,0000 pg/ml (100,000 IU/ml) of Intron A to the medium of each cell line is shown for comparison and remained constant over a 6 day period. Panel B illustrates the percentage of subdiploid cells shown 48 and 72 hours after addition of 2.5 million IU/ml of Intron A or 50 MOI of Ad-IFN-α2b. Panel C illustrates the lack of morphological changes or IFN staining in KU7 cells seen after Intron A treatment at the same concentration and time points as Panel B. In contrast, note the cells with increased size and strong perinuclear staining following treatment with Ad-IFN-α2b along with several small apoptotic appearing cells (arrows) (Magnification 40×).
Figure 5:
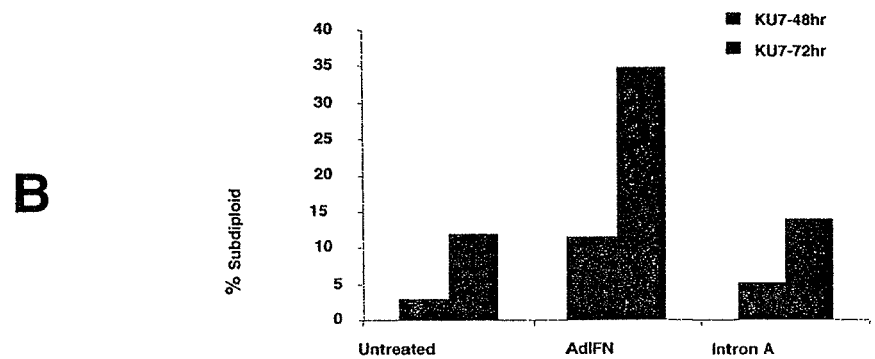
Figure 5:
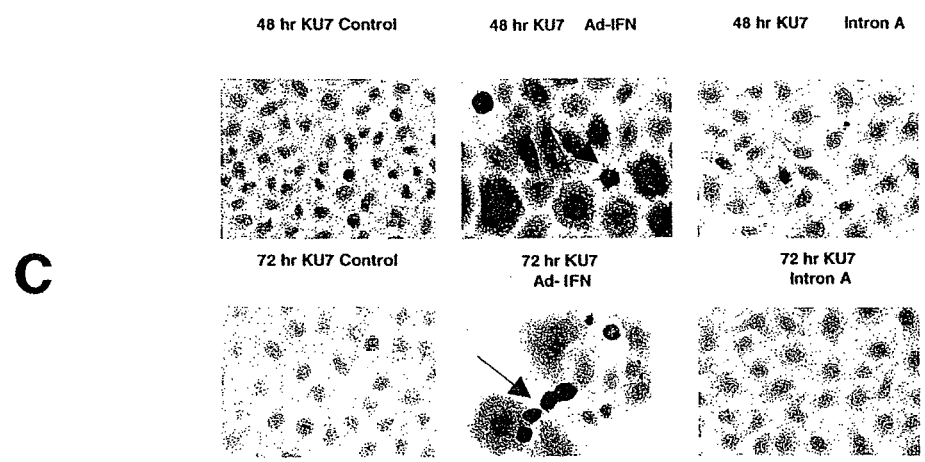

To examine the amount of IFN protein made in culture by Ad-IFN over time both KU7 and 253J B-V cells were treated with a 50 and 100 MOI of Ad-IFNα2b for 2.5 hr or with 100,000 IU/ml of Intron A. Whereas the concentration of IFN protein in the supernatant remained constant at approximately 400,000 pg/ml following Intron A (~4 pg/IU) treatment, concentrations reached almost 10,000,000 pg/ml (~2,500,000 IU) six days after treatment with 50 MOI of Ad-IFNα2b, and similar levels were documented by two days following exposure to 100 MOI of Ad-IFNα2b (FIG. 5, Panel A).

Based on these results, the effects after the addition of 2,500,000 IU/ml of Intron A were compared to that seen after treatment with a 50 MOI of Ad-IFNα2b at 48 and 72 hr. An increase in the number of subdiploid cells was found in the Ad-IFN treated cells as had been noted previously, especially at 72 hr after infection, whereas no increase was found in the cells after Intron A exposure to such a high concentration (FIG. 5, Panel B). Similarly, no morphological changes or IFN staining were seen in cells 48 and 72 hr after the Intron A exposure compared to control cells, whereas the typical morphological changes and IFN staining were found in the Ad-IFN treated cells (FIG. 5, Panel C). Nevertheless, there was a significant increase in the percentage of G2/M cells at 48 and 72 hr after Intron A treatment and this paralleled the changes seen following Ad-IFN exposure. For example, in KU7 cells the G2/M population at 48 hr after treatment for the control, Intron A and Ad-IFN groups were 9.7, 23.4 and 33.4, respectively, as well as 7.4, 21.3 and 19.5 at 72 h.

The vectors encoding both the IFNα2b and hybrid interferons clearly demonstrate that intravesical Ad-IFNα has potent antitumor activity. When tumor burden was compared before and after treatment, those tumors that received either Ad-IFNα2α1 or Ad-IFNα2b in a Syn3 formulation displayed a marked decrease in tumor size, whereas bladder tumors grew rapidly in the mice treated with Ad-β-gal/Syn3 as well as Ad-IFNα2α1, Syn3 or IFNα2α1 protein alone. Minimal local toxicity was also observed with any treatment.

Although various bladder cancer cell lines, including the KU7 cells used in the present in vivo experiments, were resistant to high levels of the IFNα protein itself in culture, they were uniformly killed in cell culture by Ad-IFNα in a caspase-dependent manner at particle concentrations that resulted in transduction of only 50% or less of cells. These results confirm that vectors encoding interferon species such as Ad-IFNα possess strong bystander effects and the ability to overcome resistance to the IFN protein.

In summary, the foregoing experiments demonstrate that recombinant vector delivered interferons possess unique properties distinct from commercially available recombinant IFN protein and that vectors encoding IFN can overcome resistance to the IFN protein. With respect to bladder cancer, the studies clearly illustrate that intravesical instillation of Ad-IFN-α2α1/Syn3 or Ad-IFN-α2b/Syn3 for one hour on consecutive days caused a marked regression in the growth of human superficial bladder tumors in athymic mice when tumor burden was determined 3 weeks after treatment. Similar treatment with 200,000 IU per day of the IFN-α2α1 protein did not result in any long-term IFN tissue levels and had no effect on the growth of the tumors. Since Ad-IFN-α2α1/Syn3 and Ad-IFN-α2b/Syn3 were comparable in producing cytotoxicity in vitro and tumor regression in vivo, the direct effect of sustained expression of IFN was a substantial factor in tumor regression rather than its effect on the tumor microenvironment in this model because IFNα2b activates only interferon signaling pathways in human cells, although it can be produced in both mouse and human cells. The data also demonstrates that Ad-IFNα can elicit caspase-dependent cytotoxicity in bladder cancer cells resistant to high concentrations of the IFN protein. Apoptosis was apparent not only in bladder cancer cells showing high intracellular levels of IFNα by immunochemical staining but also in adjacent cells that did not demonstrate IFNα expression. These results demonstrate that treatment with Ad-IFNα can produce a strong bystander effect in neighboring cells that may target tumor cells that escaped infection by Ad-IFNα.

A potential concern for the clinical application of any agent is its potential toxic side effects. However, these studies clearly demonstrate a lack of toxicity associated with the administration of recombinant vectors encoding interferon, even though there is a high, persistent interferon level produced by the vectors. The results from the foregoing studies demonstrated no significant morphological changes in the normal urothelium when the athymic mice were examined three weeks after Ad-IFNα2α1/Syn3 treatment. In addition, when nontumor-bearing normal outbred mice were similarly treated with Ad-IFNα2α1/Syn3 and examined for acute pathology in the bladder up to 21 days after exposure, no significant changes were identified upon histological examination of the bladder. In addition, pilot experiments in rats demonstrated that although interferon transgene expression was high in the urine of rats, serum concentrations were minimal indicating low systemic exposure after intravesical Ad-IFN treatment. These initial efficacy and toxicity results suggest that Ad-IFNa2b/Syn3 will be well-tolerated.

The present invention further provides pharmaceutical formulations comprising the vectors of the present invention. The compositions of the invention will be formulated for administration by manners known in the art acceptable for administration to a mammalian subject, preferably a human. In particular, delivery systems may be formulated for intramuscular, intravenous, injectable depot type devices or topical administration.

In the case where nonviral gene delivery system is employed, the expression plasmid containing the interferon gene may be encapsulated in liposomes. Liposomes include emulsions, foams, micelles, insoluble monolayers, liquid crystals, phospholipid dispersions, lamellar layers and the like. The delivery of DNA sequences to target cells using liposome carriers is well known in the art. A variety of methods are available for preparing liposomes, as described in, e.g., Szoka et al., *Ann. Rev. Biophys. Bioeng.*, 9:467 (1980), Szoka, et al., U.S. Pat. No. 4,394,448, issued Jul. 19, 1983, as well as U.S. Pat. Nos. 4,235,871, 4,501,728, 4,837,028, and 5,019,369, incorporated herein by reference. Liposomes useful in the practice of the present invention may be formed from one or more standard vesicle-forming lipids, which generally include neutral and negatively charged phospholipids and a sterol, such as cholesterol. Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEG-ylation") as described in U.S. Pat. Nos. 5,013,556, issued May 7, 1991, and 5,213,804, issued May 25, 1993.

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally," i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ.

The compositions of the invention can also be administered in topical formulations or polymer matrices, hydrogel matrices, polymer implants, or encapsulated formulations to allow slow or sustained release of the compositions. When the delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

In some applications, it is desirable to administer the recombinant vector in conjunction with enhancing agents that facilitate the transfer of the nucleic acid encoding interferon to the target cell. Examples of such delivery enhancing agents include detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Bile salts such as taurocholate, sodium tauro-deoxycholate, deoxycholate, chenodesoxycholate, glycocholic acid, glycochenodeoxycholic acid and other astringents such as silver nitrate may be used. Heparin-antagonists like quaternary amines such as protamine sulfate may also be used.

Anionic, cationic, zwitterionic, and nonionic detergents may also be employed to enhance gene transfer. Exemplary detergents include but are not limited to taurocholate, deoxycholate, taurodeoxycholate, cetylpyridium, benalkonium chloride, Zwittergent 3-14 detergent, CHAPS (3-[(3-Cholamidopropyl) dimethylammoniol]-1-propanesulfonate hydrate), Big CHAP, Deoxy Big CHAP, Triton-X-100 detergent, C12E8, Octyl-B-D-Glucopyranoside, PLURONIC-F68 detergent, Tween 20 detergent, and TWEEN 80 detergent (CalBiochem Biochemicals). Particularly preferred enhancing agents and methods are described in Engler et al., U.S. Pat. No. 6,312,681, issued Nov. 6, 2001, Engler et al., U.S. Pat. No. 6,165,779, issued Dec. 26, 2000, and Engler et al., U.S. Pat. No. 6,392,069, issued May 21, 2002, the entire teachings of which are herein incorporated by reference. A particularly preferred enhancing agent useful in the practice of the present invention is a compound termed Syn3 of the Formula I:

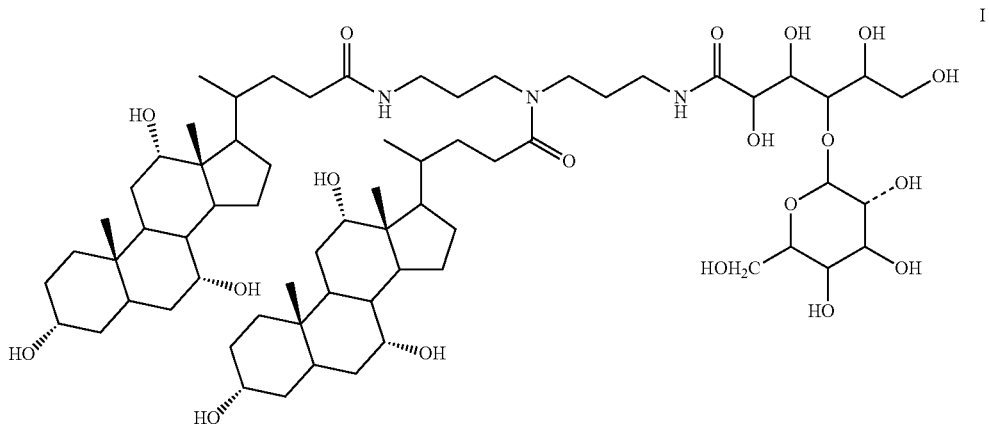 [SMILES: CC(CCC(=O)NCCCN(CCCNC(=O)C(O)C(O)C(OC1OC(CO)C(O)C(O)[C@H]1O)C(O)CO)C(=O)CCC(C)C1CCC2C3C(C[C@H](O)[C@]12C)[C@@]1(C)CC[C@@H](O)CC1C[C@H]3O)C1CCC2C3C(C[C@H](O)[C@]12C)[C@@]1(C)CC[C@@H](O)CC1C[C@H]3O]

Additional enhancing agents useful in the practice of the present invention include, but are not limited to, the compounds of the Formulas II, III, IV, and V and their pharmaceutically acceptable salts:
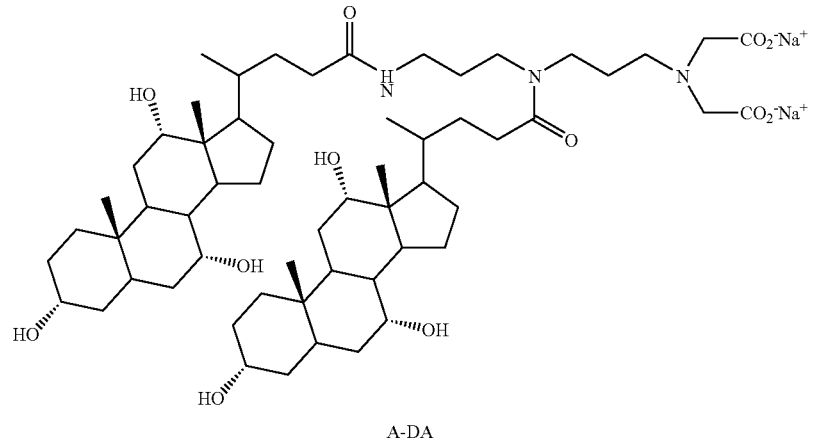
A-DA
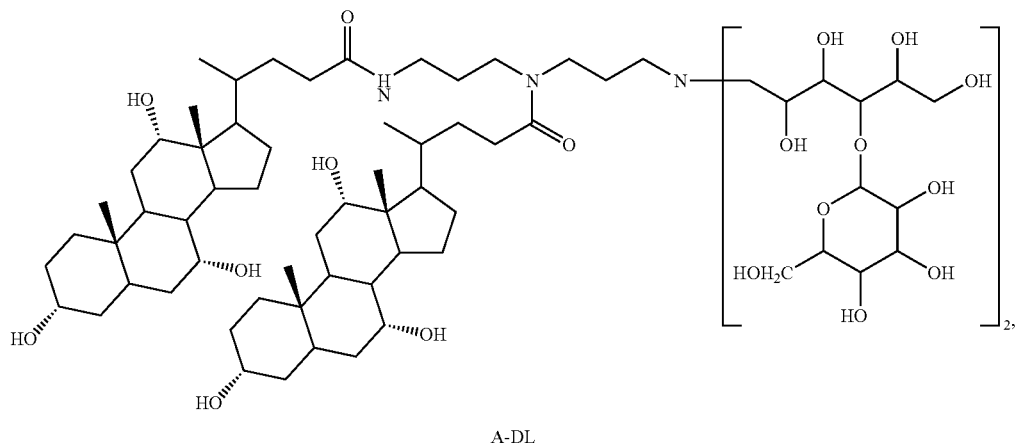
A-DL
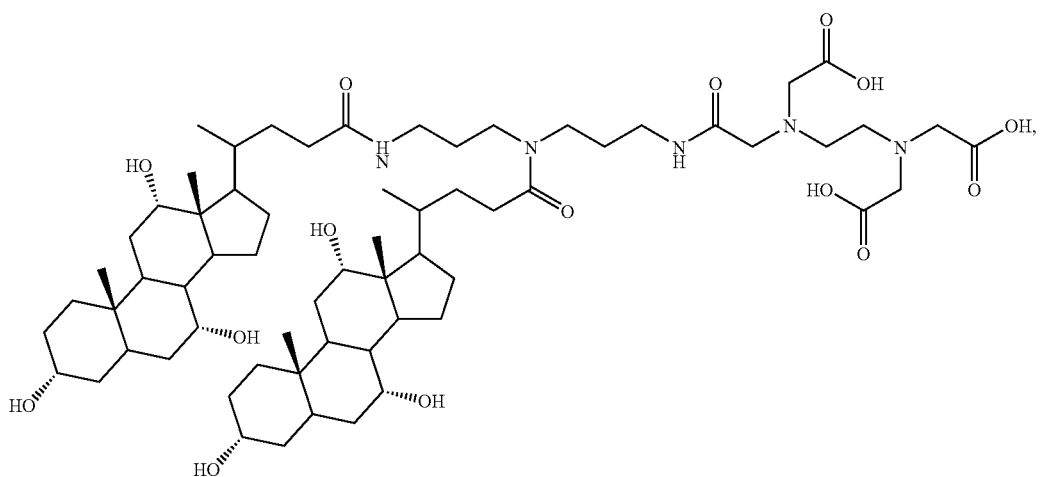

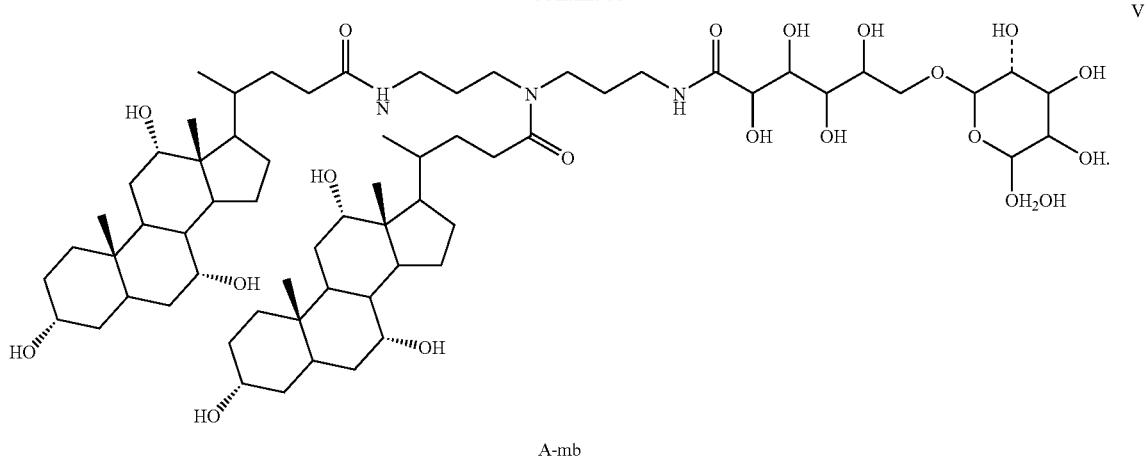

A-mb

Initial efforts to transduce the urothelium using adenovirus vectors had limited success, due in part to the presence of an anti-adherence barrier that protects against infections. Pagliaro et al., *J. Clin. Oncol.*, 15:2247-2253 (2003). An excipient, Syn3, has been identified that dramatically enhances adenovirus transduction of the urothelium. Connor et al., *Gene Ther.*, 8:41-8 (2001); Yamashita et al., *Cancer Gene Therapy*, 9:687-691 (2002). In animal models, intravesical administration of adenovirus vectors in a Syn3 formulation markedly increased transgene expression in both normal urothelium and superficial bladder tumors. The enhancing effects of Syn3 persist over a time window of approximately 1 hour. Consequently, the recombinant vectors of the present invention when used in conjunction with Syn3 are preferably administered contemporaneously and generally within a period of approximately one hour following exposure of the bladder to Syn3.

The present invention further provides a method of treating a mammalian organism containing a tumor by administering to the mammalian organism a pharmaceutical formulation comprising a recombinant vector encoding an interferon. The term "mammalian organism" includes, but is not limited to, humans, pigs, horses, cattle, dogs, and cats. When the vector is a recombinant adenoviral vector, preferably one employs an adenoviral vector endogenous to the mammalian type being treated. Although it is generally favored to employ a virus from the species to be treated, in some instances, it may be advantageous to use vectors derived from different species which possess favorable pathogenic features. For example, it is reported (PCT International Publication No. WO 97/06826, published Apr. 10, 1997) that bovine adenoviral vectors may be used in human gene therapy to minimize the immune response characteristic of human adenoviral vectors. By minimizing the initial immune response, rapid systemic clearance of the vector is avoided resulting in a greater duration of action of the vector. A pre-existing or induced immunological response to repeated in vivo administration of viral vectors has been associated with a diminished therapeutic effect of systemically administered viral vectors through multiple courses of administration. While this can be overcome by adjustments to dosage, one may also administered the vectors of the present invention in combination with immunosuppressive agents. Examples of immunosuppressive agents include, but are not limited to, cyclosporine, azathioprine, methotrexate, cyclophosphamide, lymphocyte immune globulin, antibodies against the CD3 complex, adrenocorticosteroids, sulfasalzaine, FK-506, methoxsalen, and thalidomide. Alternatively, transient elimination of antiviral antibodies may be accomplished in accordance with the teaching of La Face et al., U.S. Pat. No. 6,464,976, issued Oct. 15, 2002, the teaching of which is herein incorporated by reference.

The determination of the optimal dosage regimen for treatment of the disease will be based on a variety of factors which are within the discretion of the attending health care provider, such as the progression of the disease at the time of treatment, age, weight, sex, the type of vector being employed, whether it is being formulated with a delivery enhancing agent, the frequency of administration, etc. However, recombinant adenoviral vectors have been demonstrated to be safe and effective in human beings in the dosage range between $1 \times 10^5$ and $1 \times 10^{12}$ viral particles per dose in a multiple dosing regimen over a period of several weeks. Consequently, administration of recombinant adenoviral vectors encoding interferon may be used in such dosage ranges.

In the preferred practice of the present invention for the treatment of superficial bladder cancer in human beings, course of treatment comprising a dose of from $1 \times 10^{10}$/ml to $1 \times 10^{12}$/ml (most preferably approximately $1 \times 10^{11}$/ml) recombinant adenoviral particles encoding interferon α2b in a volume of approximately 100 ml is instilled intravesically for a period of approximately one hour. An alternate course of treatment comprises a dose of from $1 \times 10^{10}$/ml to $1 \times 10^{12}$/ml (most preferably approximately $1 \times 10^{11}$/ml) recombinant adenoviral particles encoding interferon α2b in a volume of approximately 100 ml is instilled intravesically for a period of approximately one hour followed by a second substantially equivalent dose within 7 days, 5 days, 4 days, 3 days, 2 days or on consecutive days following the first dose. Each course of treatment is repeatable, depending on the course of disease progression. In the case of intravesically administered recombinant vectors for the treatment of bladder cancer, optimal interferon gene expression is generally observed when the courses of treatment are distanced by at least 14 days, more preferably about 30 days, and most preferably about 90 days.

In the preferred practice of the invention for the treatment of hepatocellular carcinoma in a human being, a dosage regimen comprising approximately $1 \times 10^{10}$-$1 \times 10^{12}$ particles of a replication deficient recombinant adenoviral vector expressing an intracellular interferon species is administered intratumorally or via the hepatic artery for a period of five to seven consecutive days. This dosage regimen may be repeated over a course of therapy of approximately three to six weeks. A particularly preferred dosage regimen for the treatment of hepatocellular carcinoma in a human subject suffering therefrom would be to provide intrahepatic arterial administration of from approximately $1\times10^{10}$-$1\times10^{12}$ particles of a replication deficient recombinant adenoviral vector expressing inteferon-α2b under control of the AFP promoter for approximately five consecutive days. Most preferably, this dosage regimen is carried out in parallel with other chemotherapeutic regimens.

In the situation where the vector is a replication competent vector, the dosage regimen may be reduced. For example, a replication competent adenoviral vector may be constructed wherein the replication is substantially restricted to hepatocellular carcinoma cells by using the AFP promoter (for example) to drive expression of E1 proteins in lieu of the native E1 promoter. Such vector would preferentially replicate in and express interferon in tumor cells and possess the desirable ability to spread to surrounding cells expanding the therapeutic effect and allowing for a reduced dosage or shorter duration of treatment.

The compositions and methods of the present invention may be practiced alone or in combination with conventional chemotherapeutic agents or treatment regimens. Examples of such chemotherapeutic agents include inhibitors of purine synthesis (e.g., pentostatin, 6-mercaptopurine, 6-thioguanine, methotrexate) or pyrimidine synthesis (e.g., Pala, azarbine), the conversion of ribonucleotides to deoxyribonucleotides (e.g., hydroxyurea), inhibitors of dTMP synthesis (5-fluorouracil), DNA damaging agents (e.g., radiation, bleomycines, etoposide, teniposide, dactinomycine, daunorubicin, doxorubicin, mitoxantrone, alkylating agents, mitomycin, cisplatin, procarbazine) as well as inhibitors of microtubule function (e.g., vinca alkaloids and colchicine). Chemotherapeutic treatment regimens refers primarily to nonchemical procedures designed to ablate neoplastic cells such as radiation therapy. These chemotherapeutic agents may be administered separately or may be included with the formulations of the present invention for co-administration. The present invention may also be practiced in combination with conventional immunotherapeutic treatment regiments such as BCG in the case of superficial bladder cancer.

EXAMPLES

The following examples are considered illustrative of the practice of the present invention and should not be considered as limiting of the scope thereof.

Example 1

Cell Lines, Vectors, and Reagents

The bladder cancer cell lines, KU7/GFP clone 6 and 253J-B-V, were used for these studies. KU7/GFP clone 6 is stably transfected with the green-flourescent protein and was used for all in vivo studies. These cell lines are described in Watanabe et al., Cancer Gene Therapy, 7:1575-1580 (2000). The cells were grown in modified minimum essential medium supplemented with 10% FCS and incubated at 37° C. in 5% $CO_2$ and 95% air.

Recombinant adenoviral vectors encoding interferon α2α1 were prepared in substantial accordance with the teaching of Ahmed et al., Interferon Cytokine Res., 21(6): 399-408 (2001). Recombinant adenoviral vectors encoding IFN-α2b and β-galactosidase (β-gal were prepared in substantial accordance with the teaching of Ahmed et al., Hum. Gene Ther., 10 (477-8 (1999) and are also described in Gregory et al., U.S. Pat. No. 6,210,939, issued Apr. 3, 2001, the entire teaching of which is herein incorporated by reference.

Intron A protein (interferon α-2b recombinant) is commercially available from Schering Corporation.

Syn3 was prepared in substantial accordance with the teaching of Engler et al., U.S. Pat. No. 6,392,069, incorporated, supra.

Example 2

Superficial Tumor Formation, Treatment and Imaging

The methods for growing superficial KU7-GFP human bladder tumors in athymic mice and their imaging were conducted as previously been described in Izawa et al., Clin. Cancer Res, 8:1258-1270 (2002) and Zhou et al., Cancer Gene Therapy, 9:681-686 (2002). Briefly, two weeks after the tumor cells were instilled, the bladders were imaged for the presence of GFP-containing tumor. Mice then received an intravesical instillation of 100 µl of either Ad-IFN-α2α1/Syn3, Ad-IFN-α2b/Syn3, Ad-IFN-α2α1, Ad-β-gal/Syn3, Syn3 or the IFN-α2α1 protein for 1 hour. A purse-string suture was tied around the urethra to ensure retention during the procedure. Virus, Syn3 and interferon protein concentrations were $1\times10^{11}$ P/ml, 1 mg/ml and $2\times10^5$ IU/100 µl, respectively. Between 6 to 8 mice were treated per group except for Ad-IFN-α2α1/Syn3 and Ad-IFN-α2α1 groups in which 14 and 16 mice were treated, respectively.

Three weeks after the first treatment the bladder was reexposed and imaged. Following euthanasia each bladder was subsequently intravesically instilled with 100 µl of 10% formalin and the urethra sutured. The bladders were then removed, fixed in 10% formalin and embedded in paraffin blocks. Sections were then taken throughout the bladder for H & E staining to document the presence or absence of tumor, as well as to correlate the tumor imaging with histological evidence of tumor.

Example 3

Homogenate Gene Expression Studies

Female athymic mice were anesthetized, catheterized and received either a single 100 µl intravesical administration of Intron A ($2\times10^6$ IU/ml) or 1-2 daily treatments with Ad-IFN/Syn3 ($1\times10^{11}$ P/ml:1 mg/ml) for 1 hour as described above. At various intervals the bladders were harvested and frozen. The bladders were later thawed and transferred into lysis buffer (Promega). Samples were homogenized for 20 sec (Fast Prep, Q-BIOgene). The homogenates were then assayed for human interferon α protein concentration using an ELISA (Endogen). Interferon protein concentration was expressed as pg IFN/mg bladder tissue.

Example 4

Immunochemical Analysis

For in vivo studies interferon immunohistochemistry was performed in substantial accordance with the teaching of Izawa et al. above. A positive reaction was indicated by a brown staining. Similarly, interferon staining for cells in culture was performed in substantial accordance with the teaching of Xu et al., *Oncogene,* 4:807-812 (1989), except that the primary antibody used was a 1:500 dilution of rabbit polyclonal antibody against human interferon α (Hu-IFN-α, PBL).

Example 5

Statistical Analysis

Statistical analysis was performed with Image-Pro® Plus version 4.0 software for Windows (commercially available from Media Cybernetics, Inc., 8484 Georgia Avenue, Suite 200, Silver Spring, Md. 20910-5611 USA) to calculate the pixel of pre-treatment bladder area, pre-treatment GFP area, post-treatment bladder area and post-treatment GFP area. Subsequently, the percentages of pre-treatment GFP area over pre-treatment bladder area and post-treatment GFP area over post-treatment bladder area were calculated. We performed a nonparametric test (Kruskal-Wallis test) to assess differences in the percent change in tumor size among the 7 treatments as described in Kruskal and Wallis, *Journal of the American Statistical Association,* 47:583-621, Conover W J, Practical Nonparametric Statistics. 3rd ed., John Wiley & Sons, Inc., New York (1952). We used Monte-Carlo simulation to determine the p-values for the test. To adjust for the fact that we were performing many tests to compare each treatment to the others, we used a Bonferroni correction to examine the significance level for each of these tests (0.05/21=0.0024). For the MTT results, the analysis was done using the General Lineal Models of the Statistica software (commercially available from StatSoft, Inc., 2300 East 14th Street, Tulsa, Okla. 74104).

Example 6

MTT, Flow Cytometry, Caspase Activity, and Measurement of IFN in Supernatants

MTT assays were performed in substantial accordance with the teaching of Zhang et al., *Cancer Res.,* 63:760-765 (2003). Briefly, the bladder tumor cells were infected with a given adenovirus at a 50 and 100 MOI for 2.5 h. At different time points the medium was removed, and 200 μl of medium were added containing 1 mg/ml MTT. After 3 hours, the reaction was stopped with 200 μl of N,N-dimethylformamide lysis buffer, and the resultant solution read at $A^{595}$ with a microplate reader. Additional 60 mm dishes were treated similarly or with Intron A and harvested for flow cytometry and caspase activity. Supernatants from a duplicate dishes were obtained daily to measure the concentration of IFN for cells exposed to Ad-IFN-α2b or IntronA. Cell cycle analysis, percentage of subdiploid cells and caspase activity were determined in substantial accordance with the teaching of Williams et al., *Mol. Cancer. Ther.,* 2:835-843 (2003). The Intron A concentration was measured using an ELISA in accordance with the teaching of Fujisawa et al, *J. Interferon Cytokine Research,* 16:555-559 (19996) using an Endogen Brand Human IFNa ELISA kit commercially available as Catalog No. EHIFNA from Pierce Biotechnology, Inc., P.O. Box 117, 3747 N. Meridian Road, Rockford, Ill. 61105 in substantial accordance with the manufacturer's instructions.

Example 7

Confocal Microscopy Analysis for Active Caspase and IFN☐ Localization and their Correlation with Nuclear Morphological Changes Human bladder cell lines were cultured on coverslips in DMEM supplemented with 10% fetal calf serum then infected with Ad-α-gal, IFN-α2α1 or Ad-IFN-α 2b at a 50 and 100 MOI. Thirty-six hours post-infection, cells were fixed in ice-cold methanol then blocked in 10% goat serum in PBS and incubated overnight with anti-active caspase-3 monoclonal rabbit (commercially available as Catalog Number RDI-CASP3ACTabRm from Research Diagnostics Inc., Pleasant Hill Road, Flanders N.J. 07836) and anti-IFN-α monoclonal mouse (commercially available as Catalog No. 31101-1 from PBL Biomedical Laboratories, 131 Ethel Road West, Suite 6, Piscataway, N.J. 08854) antibodies at dilutions of 1:1,000 and 1:500, respectively. Alexa-488 labeled goat anti rabbit and Alexa-546 labeled goat anti-mouse antibodies (commercially available as Catalog Nos. 11101 and 11010, respectively, from Molecular Probes, 29851 Willow Creek Road, Eugene, Oreg. 97402) were then added together with the DNA dye, 633-Topro-3 (commercially available from Molecular Probes) for another hour. Mounted slides were imaged using a confocal microscope (Zeiss model LSM-510) and pixels were analyzed in each channel using Argon and He/Ne lasers equipped with appropriate optical filters. The images are representative for at least ten microscopic fields analyzed for each condition. Each experiment was performed in duplicate and repeated at least three times.

What is claimed is:

1. A method of treating an interferon-resistant lung cancer by contacting said cancer with a recombinant vector encoding an interferon.

2. The method of claim 1 wherein said recombinant vector is an adenovirus.

3. The method of claim 2 wherein said adenovirus is replication deficient.

4. The method of claim 3 wherein said interferon is an interferon α.

5. The method of claim 4 wherein said interferon alpha is selected from the group consisting of interferon α2b, interferon α2a, and interferon α2α1.

6. The method of claim 1 wherein cells of said interferon-resistant lung cancer have been exposed to an enhancing agent.

7. The method of claim 6 where in the enhancing agent is Syn3.

8. The method of claim 7 wherein said vector and sand enhancing agent are administered together.

9. The method of claim 7 wherein said interferon is interferon α2b.

10. The method of claim 7 wherein said vector and sand enhancing agent are administered contemporaneously.

11. The method of claim 7 wherein said vector is administered within an hour after administering the enhancing agent.

12. The method of claim 7 wherein said vector and said enhancing agent are administered by inhalation.

13. The method of claim 7 wherein said vector and said enhancing agent are administered intralesionally.

* * * * *